(12) United States Patent
Matsushima et al.

(10) Patent No.: US 11,185,851 B2
(45) Date of Patent: *Nov. 30, 2021

(54) POLYMER-SUPPORTED METAL

(71) Applicant: TAKASAGO INTERNATIONAL CORPORATION, Tokyo (JP)

(72) Inventors: Yoshimasa Matsushima, Hiratsuka (JP); Takashi Ohshima, Fukuoka (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 296 days.

This patent is subject to a terminal disclaimer.

(21) Appl. No.: 16/074,473

(22) PCT Filed: Feb. 16, 2017

(86) PCT No.: PCT/JP2017/005747
§ 371 (c)(1),
(2) Date: Aug. 1, 2018

(87) PCT Pub. No.: WO2017/142028
PCT Pub. Date: Aug. 24, 2017

(65) Prior Publication Data
US 2019/0060887 A1 Feb. 28, 2019

(30) Foreign Application Priority Data

Feb. 16, 2016 (JP) ............... JP2016-026689

(51) Int. Cl.
| | | |
|---|---|---|
| *B01J 31/16* | (2006.01) |
| *C07J 9/00* | (2006.01) |
| *C07D 473/16* | (2006.01) |
| *C07C 68/06* | (2020.01) |
| *C07C 69/96* | (2006.01) |
| *C07C 43/23* | (2006.01) |
| *C07C 69/145* | (2006.01) |
| *C07C 31/125* | (2006.01) |
| *C07C 33/32* | (2006.01) |
| *C07C 201/12* | (2006.01) |
| *B01J 31/06* | (2006.01) |
| *C07C 33/02* | (2006.01) |
| *C07C 205/43* | (2006.01) |
| *C07C 213/06* | (2006.01) |
| *C07C 219/14* | (2006.01) |
| *C07C 67/03* | (2006.01) |
| *C07C 39/20* | (2006.01) |
| *C07C 69/24* | (2006.01) |
| *C07C 33/22* | (2006.01) |
| *C07C 69/78* | (2006.01) |
| *C07F 7/18* | (2006.01) |
| *C07D 317/38* | (2006.01) |
| *C07C 69/14* | (2006.01) |
| *C07C 37/055* | (2006.01) |
| *C07C 41/16* | (2006.01) |
| *C07C 69/157* | (2006.01) |
| *B01J 37/04* | (2006.01) |

(Continued)

(52) U.S. Cl.
CPC .......... *B01J 31/1658* (2013.01); *B01J 31/06* (2013.01); *B01J 37/04* (2013.01); *C07C 29/1285* (2013.01); *C07C 31/125* (2013.01); *C07C 33/02* (2013.01); *C07C 33/22* (2013.01); *C07C 33/32* (2013.01); *C07C 37/055* (2013.01); *C07C 37/0555* (2013.01); *C07C 39/20* (2013.01); *C07C 41/16* (2013.01); *C07C 43/23* (2013.01); *C07C 67/02* (2013.01); *C07C 67/03* (2013.01); *C07C 67/08* (2013.01); *C07C 68/06* (2013.01); *C07C 69/14* (2013.01); *C07C 69/145* (2013.01); *C07C 69/157* (2013.01); *C07C 69/24* (2013.01); *C07C 69/78* (2013.01); *C07C 69/96* (2013.01); *C07C 201/12* (2013.01); *C07C 205/43* (2013.01); *C07C 213/06* (2013.01); *C07C 219/14* (2013.01); *C07D 317/36* (2013.01); *C07D 317/38* (2013.01); *C07D 473/16* (2013.01); *C07F 7/18* (2013.01); *C07J 9/00* (2013.01); *C07B 61/00* (2013.01); *Y02P 20/584* (2015.11)

(58) Field of Classification Search
None
See application file for complete search history.

(56) References Cited

U.S. PATENT DOCUMENTS

2009/0198070 A1 8/2009 Mashima et al.
2010/0249422 A1 9/2010 Mashima et al.
(Continued)

FOREIGN PATENT DOCUMENTS

JP 60-096601 A 5/1985
JP 2009-185033 A 8/2009
(Continued)

OTHER PUBLICATIONS

Machine Translation of JP-S60-96601, published May 1985 (Year: 1985).*
Kim, D., Kim, M., Roshith, K. et al. Comparative catalytic activity of supported ZnBr2-containing ionic liquid catalysts for preparation of glycerol carbonate by glycerolysis of urea. Korean J. Chem. Eng. 31, 972-980 (2014). https://doi.org/10.1007/s11814-013-0296-0 (Year: 2014).*
Collman et al. (ACS, 1974, 6800-6802 (Year: 1974).*
(Continued)

Primary Examiner — Yun Qian
(74) Attorney, Agent, or Firm — Sughrue Mion, PLLC

(57) ABSTRACT

A macromolecules containing a metal and a use thereof as a catalyst are disclosed. The macromolecules containing a metal may be obtained by causing a ligand to react with a zinc compound or a cobalt compound. The ligand has an imidazole group that is bonded to a macromolecule via a linker. The metal-containing macromolecules are highly active as a catalyst, stable, and easy to recover and reuse.

2 Claims, 2 Drawing Sheets

(51) Int. Cl.
*C07C 29/128* (2006.01)
*C07C 67/02* (2006.01)
*C07C 67/08* (2006.01)
*C07D 317/36* (2006.01)
*C07B 61/00* (2006.01)

(56) References Cited

U.S. PATENT DOCUMENTS

| | | |
|---|---|---|
| 2011/0098479 A1 | 4/2011 | Mashima et al. |
| 2012/0172601 A1 | 7/2012 | Matsushima et al. |
| 2013/0190502 A1 | 7/2013 | Mashima et al. |
| 2016/0002268 A1 | 1/2016 | Ohshima et al. |

FOREIGN PATENT DOCUMENTS

| | | | | |
|---|---|---|---|---|
| JP | 2011-079810 A | 4/2011 | | |
| KR | 2010121735 A | * 11/2010 | ............. | B01J 31/06 |
| WO | 2009/047905 A1 | 4/2009 | | |
| WO | 2014/157524 A1 | 10/2014 | | |

OTHER PUBLICATIONS

Takanori Iwasaki et al., "Transesterification of Various Methyl Esters Under Mild Conditions Catalyzed by Tetranuclear Zinc Cluster", J. Org. Chem., 2008, pp. 5147-5150, vol. 73, No. 13.
Takeshi Ohshima et al., "Enzyme-Like Chemoselective Acylation of Alcohols in the Presence of Amines Catalyzed by a Tetranuclear Zinc Cluster", J. Am. Chem. Soc., 2008, pp. 2944-2945, vol. 130, No. 10.
Takanori Iwaski et al., "A Simple, General, and Highly Chemoselective Acetylation of Alcohols Using Ethyl Acetate as the Acetyl Donor Catalyzed by a Tetranuclear Zinc Cluster", Synlett, 2009, pp. 1659-1663, No. 10.
Takanori Iwaski et al., "A Tetranuclear-Zinc-Cluster-Catalyzed Practical and Versatile Deprotection of Acetates and Benzoates", Chem. Eur. J., 2010, pp. 11567-11571, 16.
Yusuke Maegawa et al., "Additive Effect of N-Heteroaromatics on Transesterification Catalyzed by Tetranuclear Zinc Cluster", ACS Catal., 2011, pp. 1178-1182, 1.
Daiki Nakatake et al., "A highly stable but highly reactive zinc catalyst for transesterification supported by a bis(imidazole) ligand", Green Chem., Advance Article, 2016. 7 pages.
Daiki Nakatake et al., "A highly stable but highly reactive zinc catalyst for transesterification supported by a bis(imidazole) ligand", Green Chem., 2016, pp. 1524-1530, 18.
Daiki Nakatake et al., "Transesterifieation Reactions Catalyzed by a Recyclable Heterogeneous Zinc/Imidazole Catalyst", Adv. Synth. Catal., 2016, pp. 2569-2574, 358.
International Search Report for PCT/JP2017/005747, dated May 23, 2017.
Lixia Li et al., "Polvstyrene-supported CuI-imidazole complex catalyst for aza-Michael reaction of imidazoles with α,β-unsaturated compounds", Journal of Molecular Catalysis A: Chemical, vol. 353-354 (2012) pp. 178-184 (7 pages total).
Extended European Search Report dated Jan. 27, 2020, issued by the European Patent Office in Application No. 17753283.5.

* cited by examiner

POLYMER-SUPPORTED METAL

This Application is a National Stage of International Application No. PCT/JP2017/005747 filed Feb. 16, 2017, claiming priority based on Japanese Patent Application No. 2016-026689 filed Feb. 16, 2016.

TECHNICAL FIELD

The present invention relates to a novel polymer-supported metal useful as, for example, a catalyst for transesterification reaction, esterification reaction, carbonate formation reaction, and the like.

BACKGROUND ART

Many metal complexes having metal atom in their molecules have been proposed and developed as highly-active catalysts. Among these, catalysts comprising trifluoroacetate-bridged zinc tetranuclear cluster complexes containing four zinc ions are excellent catalysts that promote various reactions such as transesterification reaction, hydroxy group-selective acylation reaction in the presence of an amino group, acetylation reaction, deacetylation reaction, direct oxazoline formation reaction from a carbonyl compound, and amidation reaction in an environmentally friendly manner with low formation of by-products (for example, Non Patent Literatures 1 to 5, Patent Literatures 1 to 3).

The above-described catalysts, which are homogeneous catalysts, exhibit high activity and high selectivity, but are sensitive to moisture, and tend to be deactivated during reaction. For this reason, the catalysts present a problem in recycling. In addition, removal of the zinc metal after reaction may present a problem in some cases.

As a solution to solve the above-described problems, there is a ladder zinc catalyst obtained by mixing a bidentate ligand in which two imidazole groups are linked to each other through a suitable linker with a zinc carboxylate compound (Non Patent Literature 6, Patent Literature 4).

The above-described ladder zinc catalyst can be precipitated and separated by adding a poor solvent after reaction. However, the zinc catalyst may be difficult to remove depending on the solvent. Especially when a catalyst is used for a flow reaction or the like, the catalyst is desirably a solid, which form a heterogeneous system.

On the other hand, some solid catalysts exhibit activities for similar reactions. However, the chemical structures of such solid catalysts are not necessarily well defined, and are difficult to tune by changing the structures. As a method for achieving satisfactorily high activity, stability, and recyclability by incorporating features of the both, there is a method in which a homogeneous catalyst is immobilized to a solid phase. However, this method is yet to achieve sufficient performance.

CITATION LIST

Patent Literatures

Patent Literature 1: Japanese Patent Application Publication No. 2009-185033
Patent Literature 2: Domestic Re-publication of PCT International Publication No. 2009-047905
Patent Literature 3: Japanese Patent Application Publication No. 2011-079810
Patent Literature 4: WO2014/157524

Non Patent Literatures

Non Patent Literature 1: J. Org. Chem., 2008, 73, 5147
Non Patent Literature 2: J. Am. Chem. Soc., 2008, 130, 2944
Non Patent Literature 3: Synlett, 2009, 10, 1659
Non Patent Literature 4: Chem, Eur, J., 2010, 16, 11567
Non Patent Literature 5: ACS Catal., 2011, 1, 1178
Non Patent Literature 6: Green Chem., 2016, Advance Article

SUMMARY OF INVENTION

An object of the present invention is to solve the above-described problems of metal catalysts, and to provide a novel polymer-supported metal catalyst which is highly active as a catalyst, stable, and further easy to recover and reuse.

To achieve the above-described object, the present inventors have conducted intensive study, and consequently have found that a polymer-supported metal catalyst that achieves the above-described object can be obtained, when a ligand in which an imidazole group is linked to a polymer through a suitable linker is mixed with a metal inorganic salt, a metal carboxylate compound, or a mixture of both a metal inorganic salt and a metal carboxylate at an suitable ratio.

The present invention relates to the following [1] to [8].
[1] A polymer-supported metal, on which zinc or cobalt is supported, obtained by reacting, in a solvent, a zinc compound or a cobalt compound with a polymer represented by the following general formula (I):

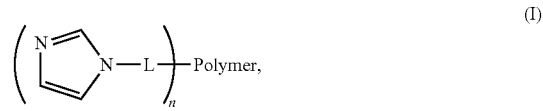

wherein Polymer represents a polymer backbone, L represents a linker moiety, and n represents a natural number.
[2] The polymer-supported metal according to the above-described [1], wherein
Polymer in formula (I) of the above-described [1] is polystyrene, and
L in formula (I) of the above-described [1] is a methylene group.
[3] A catalyst comprising the polymer-supported metal according to the above-described [1] and [2].
[4] A method for acylating a hydroxy group with a carboxylic acid or an ester thereof, comprising using the catalyst according to the above-described [3].
[5] A method for deacylating a carboxylic acid ester, comprising using the catalyst according to the above-described [3].
[6] A method for carbonate formation, comprising reacting a carbonic acid ester with an alcohol by using the catalyst according to the above-described [3].
[7] A method for producing the polymer-supported metal according to the above-described [1] or [2], the method comprising reacting a zinc compound or cobalt compound represented by the following general formula (II):

wherein X represents an optionally halogen atom-substituted alkanoyloxy group having 2 to 5 carbon atoms, a halogen atom, and a trifluoromethanesulfonyloxy group, x represents an integer, and M represents a zinc or cobalt atom, with a polymer represented by the following general formula (I):

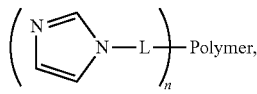

wherein Polymer represents a polymer backbone, L represents a linker moiety, and n represents a natural number.

[8] A method for producing the polymer-supported metal according to the above-described [1] or [2], the method comprising reacting a zinc tetranuclear cluster compound represented by the following general formula (III):

$$Zn_4O(OCOR)_6(RCOOH)_n \quad (III),$$

wherein R represents an optionally halogen atom-substituted alkyl group having 1 to 4 carbon atoms, and n represents 0 to 1,
with a polymer represented by the following general formula (I):

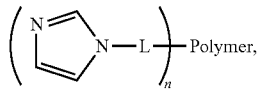

wherein Polymer represents a polymer backbone, L represents a linker moiety, and n represents a natural number.

The polymer-supported metal of the present invention is highly active as a catalyst, stable, and further easy to recover and reuse. Especially, the catalyst, i.e., the metal can be easily removed after reaction. This makes it possible to conduct a reaction in a manner excellent in environmental friendliness, handleability, and further economic efficiency. Moreover, the polymer-supported metal of the present invention is also useful as a catalyst for synthesis of pharmaceutical or agrochemical intermediates, functional materials, structural materials, and the like.

DESCRIPTION OF EMBODIMENTS

Figure 1:
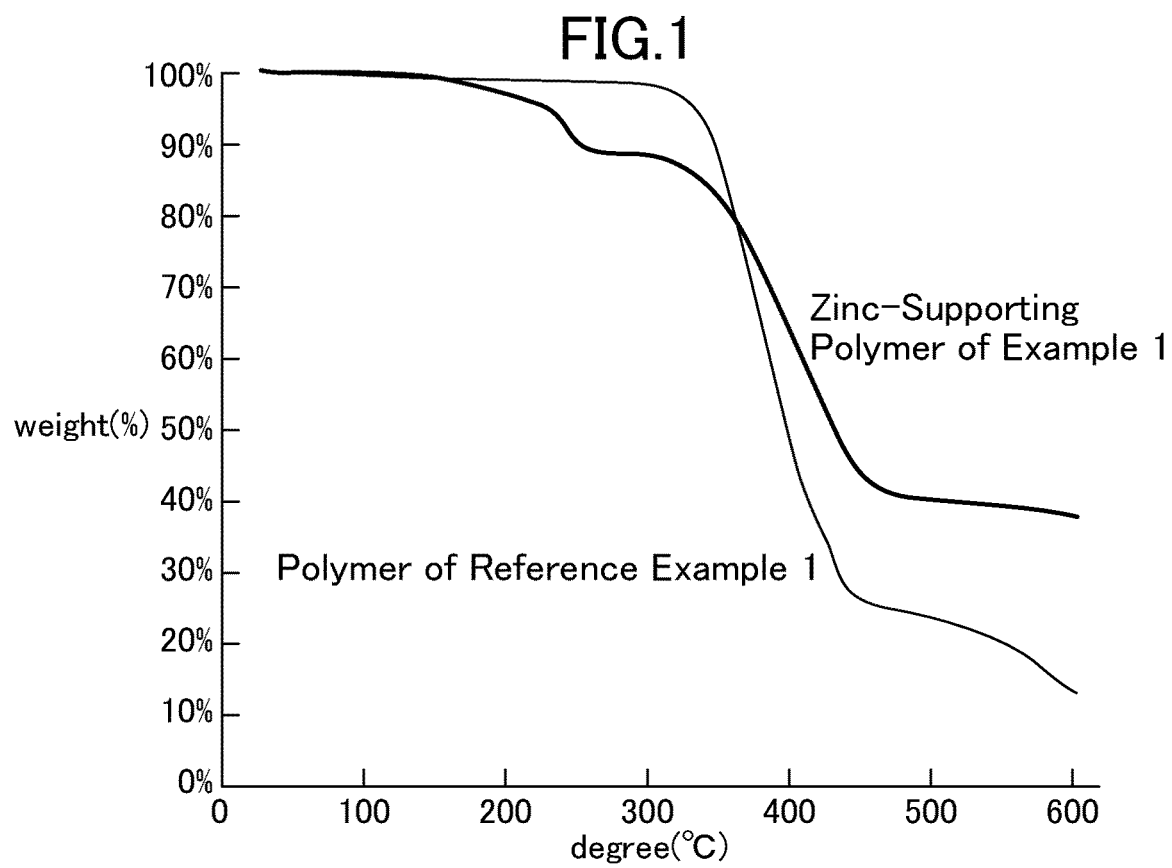
FIG. 1 is a graph showing the results obtained when a polymer-supported zinc prepared in Example 1 and an imidazolyl group-containing polymer synthesized in Reference Example 1 were subjected to simultaneous thermogravimetry/differential thermal analysis measurement (TG/DTA) in nitrogen gas at 10 mL/min.

Hereinafter, the present invention will be described specifically.

A polymer-supported metal of the present invention is obtained by reacting a polymer compound represented by general formula (I) and having imidazolyl groups linked to a polymer main chain through a linker L, with a zinc or cobalt compound.

Divalent groups represented by the linker moiety L include linear or branched alkylene groups having 1 to 20 carbon atoms, cycloalkylene groups having 3 to 8 carbon atoms, linear or branched alkenylene groups having 2 to 20 carbon atoms, cycloalkenylene groups having 3 to 20 carbon atoms, linear or branched alkynylene groups having 2 to 20 carbon atoms, arylene groups having 6 to 20 carbon atoms, aralkylene groups having 7 to 20 carbon atoms, heteroalkylene groups having 1 to 20 carbon atoms, heteroarylene groups having 2 to 20 carbon atoms, heteroaralkylene groups having 3 to 20 carbon atoms, phenylenevinylene groups, polyfluorenediyl groups, polythiophenediyl, dialkylsilanediyl groups, and diarylsilanediyl groups, and groups derived from derivatives thereof. These divalent groups may have substituents, and two or more of these groups of atoms may be combined with one another.

Examples of the linear or branched alkylene groups having 1 to 20 carbon atoms include linear alkylene groups such as methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups; branched alkylene groups such as propylene, methylpropanediyl, 1,2-butanediyl, 1,2-dimethylethylene, 1,1-dimethylethylene, 1-ethylpropylene, 2-ethylpropylene, 1,2-dimethylpropylene, 2,2-dimethylpropylene, 1-propylpropylene, 2-propylpropylene, 1-methyl-1-ethylpropylene, 1-methyl-2-ethyl-propylene, 1-ethyl-2-methyl-propylene, 2-methyl-2-ethyl-propylene, 1-methylbutylene, 2-methylbutylene, 3-methylbutylene, 2-ethylbutylene, methylpentylene, ethylpentylene, methylhexylene, methylheptylene, methyloctylene, methylnonylene, methyldecylene, methylundecylene, methyldodecylene, methyltetradecylene, and methyloctadecylene groups; and the like. Preferred are linear alkylene groups having 1 or 2 carbon atoms, and more preferred is a methylene group. In addition, these alkylene groups may have substituents described later.

The cycloalkylene groups having 3 to 8 carbon atoms include a cyclopropylene group, a cyclobutylene group, a cyclopentylene group, a cyclohexylene group, a cycloheptylene group, a cyclooctylene group, 1,2-cyclohexylenebismethylene, 1,3-cyclohexylenebismethylene, 1,4-cyclohexylenebismethylene, and the like. These cycloalkylene groups may have substituents described later.

Examples of the linear or branched alkenylene groups having 2 to 20 carbon atoms include vinylene, 1-methylethenediyl, propenylene, 2-butenylene, 2-pentenylene, 3-pentenylene, and the like. These alkenylene groups may have substituents described later.

Examples of the cycloalkenylene groups having 3 to 20 carbon atoms include cyclopropenylene, cyclobutenylene, cyclopentenylene, cyclohexenylene, and cyclooctenylene groups, and the like. These cycloalkenylene groups may have substituents described later.

Examples of the linear or branched alkynylene groups having 2 to 20 carbon atoms include ethynylene, propynylene, 3-methyl-1-propynylene, butynylene, 1,3-butadiynylene, pentynylene, 2-pentynylene, 2,4-pentadiynylene, 2-hexynylene, 1,3,5-hexatriynylene, 3-heptynylene, 4-octynylene, 4-nonynylene, 5-decynylene, 6-undecynylene, and 6-dodecynylene groups, and the like. These alkynylene groups may have substituents.

Examples of the arylene groups having 6 to 20 carbon atoms include phenylene (o-phenylene, m-phenylene, and p-phenylene), biphenylene, naphthalenediyl, binaphthalenediyl, anthracenediyl, and phenanthrenediyl groups, and the like. These arylene groups may have substituents described later.

The aralkylene groups having 7 to 20 carbon atoms include groups represented by —CH$_2$—Z—(CH$_2$-)a, where Z represents phenylene, naphthalenediyl, or biphenylene, and a represents 0 or 1. Specific examples of the groups include phenylenemethylene (o-phenylenemethylene, m-phenylenemethylene, and p-phenylenemethylene), phenylenebismethylene (1,2-phenylenebismethylene, 1,3-phenylenebismethylene, and 1,4-phenylenebismethylene), naphthalenediylbismethylene, biphenylenebismethylene, and the like. These aralkylene groups may have substituents described later.

The heteroalkylene groups having 1 to 20 carbon atoms mean the same groups as the above-described alkylene groups, except that one or more, desirably one to five carbon atoms in the main chain in the alkylene groups are substituted with heteroatoms such as oxygen atoms, sulfur atoms, nitrogen atoms, and phosphorus atoms. Examples thereof include alkyleneoxy, alkylenedioxy, alkyleneamino, and alkylenediamino. These heteroalkylene groups may have substituents described later.

The heteroarylene groups having 2 to 20 carbon atoms mean the same groups as the above-described arylene groups, except that one or more, desirably one to five carbon atoms of the arylene groups are substituted with heteroatoms such as oxygen atoms, sulfur atoms, nitrogen atoms, and phosphorus atoms. These heteroarylene groups may have substituents described later.

The heteroaralkylene groups having 3 to 20 carbon atoms mean the same groups as the above-described aralkylene groups, except that one or more, desirably one to five carbon atoms of the aralkylene groups are substituted with heteroatoms such as oxygen atoms, sulfur atoms, nitrogen atoms, and phosphorus atoms. Preferred examples thereof include those having a structure such as —CH$_2$—Z—CH$_2$—, where Z is a divalent group derived from furan, pyrrole, thiophene, pyridine, pyrazole, or imidazole. These heteroarylalkylene groups may have substituents described later.

Among the divalent groups represented by linker moiety L shown as examples above, preferred are linear or branched optionally substituted alkylene groups having 1 to 20 carbon atoms, optionally substituted arylene groups, optionally substituted heteroalkylene groups, optionally substituted aralkylene groups, or optionally substituted heteroaralkylene groups. Further preferred are optionally substituted aralkylene groups or optionally substituted heteroaralkylene groups, and most preferred are optionally substituted aralkylene groups. Further preferred are a methylene group and a p-phenylenemethylene group.

Examples of substituents which may be present on the above-described divalent groups include alkyl groups, alkenyl groups, alkynyl groups, aryl groups, aliphatic heterocyclic groups, aromatic heterocyclic groups, hydroxyl groups which may be protected with protective groups (for example, alkoxy groups, alkylenedioxy groups, aryloxy groups, aralkyloxy groups, and heteroaryloxy groups), hydroxymethyl groups which may be protected with protective groups, acyl groups, substituted amino groups (for example, alkyl-substituted amino groups, aryl-substituted amino groups, aralkyl-substituted amino groups, acyl-substituted amino groups, and alkoxycarbonyl-substituted amino groups), carboxyl groups which may be protected with protective groups (for example, alkoxycarbonyl groups, aryloxycarbonyl groups, and aralkyloxycarbonyl groups), sulfo groups, oxo groups, cyano groups, nitro groups, halogenated alkyl groups, halogen atoms, and the like. As the protective groups, protective groups commonly used in the field of organic synthesis can be used.

The alkyl groups includes alkyl groups which may be linear, branched, or cyclic and which have, for example, 1 to 15 carbon atoms, preferably 1 to 10 carbon atoms, and more preferably 1 to 6 carbon atoms, and specifically include methyl, ethyl, n-propyl, isopropyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, 2-methylpentyl, 3-methylpentyl, 4-methylpentyl, 2-methylpentan-3-yl, cyclopropyl, cyclobutyl, cyclopentyl, and cyclohexyl groups, and the like. The alkenyl groups include alkenyl groups which may be linear or branched and which have, for example, 2 to 15 carbon atoms, preferably 2 to 10 carbon atoms, and more preferably 2 to 6 carbon atoms, and specifically include vinyl, 1-propenyl, allyl, 1-butenyl, 2-butenyl, 1-pentenyl, 2-pentenyl, and hexenyl groups, and the like.

The alkynyl groups include alkynyl groups which may be linear or branched and which have, for example, 2 to 15 carbon atoms, preferably 2 to 10 carbon atoms, and more preferably 2 to 6 carbon atoms, and specifically include ethynyl, 1-propynyl, 2-propynyl, 1-butynyl, 3-butynyl, pentynyl, and hexynyl groups, and the like.

The aryl groups include aryl groups having, for example, 6 to 14 carbon atoms, and specifically include phenyl, naphthyl, anthryl, phenanthrenyl, and biphenyl groups, and the like.

The aliphatic heterocyclic groups include 5 to 8-membered, preferably 5 or 6-membered monocyclic aliphatic heterocyclic groups which have, for example, 2 to 14 carbon atoms, and which contain at least one, preferably one to three heteroatoms such as nitrogen atoms, oxygen atoms, and sulfur atoms, and polycyclic or fused-cyclic aliphatic heterocyclic groups. Specific examples of the aliphatic heterocyclic groups include, for example, pyrrolidyl-2-one, piperidino, piperazinyl, morpholino, tetrahydrofuryl, tetrahydropyranyl, and tetrahydrothienyl groups, and the like.

The aromatic heterocyclic groups include 5 to 8-membered, preferably 5 or 6-membered monocyclic aromatic heterocyclic groups which have, for example, 2 to 15 carbon atoms and which contains at least one, preferably one to three heteroatoms such as nitrogen atoms, oxygen atoms, and sulfur atoms, and polycyclic or fused-cyclic aromatic heterocyclic groups, and specifically include furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzoimidazolyl, benzoxazolyl, and benzothiazolyl groups, and the like.

The alkoxy groups include alkoxy groups which may be linear, branched, or cyclic, and which have, for example, 1 to 6 carbon atoms, and specifically include methoxy, ethoxy, n-propoxy, isopropoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, and cyclohexyloxy groups, and the like.

The alkylenedioxy groups include alkylenedioxy groups having, for example, 1 to 3 carbon atoms, and specifically include methylenedioxy, ethylenedioxy, and propylenedioxy groups, and the like.

The aryloxy groups include aryloxy groups having, for example, 6 to 14 carbon atoms, and specifically include phenyloxy, naphthyloxy, anthryloxy, and benzyloxy groups, and the like.

The aralkyloxy groups include aralkyloxy groups having, for example, 7 to 12 carbon atoms, and specifically include benzyloxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, and 6-phenylhexyloxy groups, and the like.

The heteroaryloxy groups include heteroaryloxy groups which contain, for example, at least one, preferably one to three heteroatoms such as nitrogen atoms, oxygen atoms, and sulfur atoms, and which have 2 to 14 carbon atoms, and specifically include 2-pyridyloxy, 2-pyrazyloxy, 2-pyrimidyloxy, and 2-quinolyloxy groups, and the like.

The alkoxycarbonyl groups include alkoxycarbonyl groups which may be linear, branched, or cyclic and which have, for example, 2 to 19 carbon atoms, and specifically include methoxycarbonyl, ethoxycarbonyl, n-propoxycarbonyl, isopropoxycarbonyl, n-t-butoxycarbonyl, tert-t-butoxycarbonyl, pentyloxycarbonyl, hexyloxycarbonyl, 2-ethylhexyloxycarbonyl, lauryloxycarbonyl, stearyloxycarbonyl, and cyclohexyloxycarbonyl groups, and the like.

The aryloxycarbonyl groups include aryloxycarbonyl groups having, for example, 7 to 20 carbon atoms, and specifically include phenoxycarbonyl and naphthyloxycarbonyl groups, and the like. The aralkyloxycarbonyl groups include aralkyloxycarbonyl groups having, for example, 8 to 15 carbon atoms, and specifically include benzyloxycarbonyl and phenylethoxycarbonyl groups, 9-fluorenylmethyloxycarbonyl, and the like.

The aralkyloxycarbonyl groups include aralkyloxycarbonyl groups having, for example, 8 to 15 carbon atoms, and specifically include benzyloxycarbonyl and phenylethoxycarbonyl groups, 9-fluorenylmethyloxycarbonyl, and the like.

The acyl groups include acyl groups having 1 to 18 carbon atoms which may be linear or branched and which are derived from carboxylic acids such as fatty acid carboxylic acids or aromatic carboxylic acids, and specific examples thereof include formyl, acetyl, propionyl, acryloyl, butyryl, pivaloyl, pentanoyl, hexanoyl, lauroyl, stearoyl, and benzoyl groups, and the like.

The substituted amino groups include amino groups of which one or two hydrogen atoms are substituted with substituents such as the above-described alkyl groups, the above-described aryl groups, or protective groups for amino groups. As the protective groups, any protective groups used as amino-protecting groups can be used (see, for example, PROTECTIVE GROUPS IN ORGANIC SYNTHESIS THIRD EDITION (JOHN WILEY & SONS, INC. (1999))). Specific examples of the amino-protecting groups include aralkyl groups having 7 to 20 carbon atoms, acyl groups having 1 to 8 carbon atoms, alkoxycarbonyl groups having 2 to 5 carbon atoms, aryloxycarbonyl groups having 6 to 20 carbon atoms, aralkyloxycarbonyl groups having 7 to 12 carbon atoms, and the like.

Specific examples of the alkyl group-substituted amino groups include monoalkylamino or dialkylamino groups such as N-methylamino, N,N-dimethylamino, N,N-diethylamino, and N,N-diisopropylamino groups, and N-cyclohexylamino groups.

Specific examples of the aryl group-substituted amino groups include monoarylamino or diarylamino groups such as N-phenylamino, N-(3-tolyl)amino, N,N-diphenylamino, N,N-di(3-tolyl)amino, N-naphthylamino, and N-naphthyl-N-phenylamino groups.

Specific examples of the amino groups substituted with aralkyl groups, i.e., aralkyl group-substituted amino groups include monoaralkylamino or diaralkylamino groups such as N-benzylamino groups and N,N-dibenzylamino groups.

Specific examples of the acyl group-substituted amino groups include formylamino, acetylamino, propionylamino, pivaloylamino, pentanoylamino, hexanoylamino, and benzoylamino groups, and the like.

Specific examples of the alkoxycarbonyl group-substituted amino groups include methoxycarbonylamino, ethoxycarbonylamino, n-propoxycarbonylamino, n-butoxycarbonylamino, tert-butoxycarbonylamino, pentyloxycarbonylamino, and hexyloxycarbonylamino groups, and the like.

Specific examples of the aryloxycarbonyl group-substituted amino groups include phenoxycarbonylamino and naphthyloxycarbonylamino groups, and the like.

Specific examples of the aralkyloxycarbonyl group-substituted amino groups include a benzyloxycarbonylamino group and the like.

The halogenated alkyl groups include groups which are the same as alkyl groups having 1 to 4 carbon atoms, except that a hydrogen atom(s) is substituted with a halogen atom described later, and examples thereof include fluoromethyl, difluoromethyl, trifluoromethyl, and trichloromethyl groups, and the like.

The halogen atoms include fluorine atoms, chlorine atoms, bromine atoms, iodine atoms, and the like.

Polymer in formula (I) represents a polymer backbone. The polymer backbone may be formed from any monomer, as long as the polymer backbone can bond to the linker L.

Specific polymer backbone include those derived from polymer compounds such as polyethylene, polypropylene, nylon, polyacrylate, polymethacrylate, polyamide, polyacrylonitrile, polyvinyl chloride, polyvinyl acetate, polyphenol resin, epoxy resin, polyester, alkyd resin, polycarbonate, polyurethane, polystyrene, polyvinylcarbazole, polyvinylanthracene, and polyvinylene, and copolymers thereof.

As for preferred polymer compounds, preferred are cross-linkable polymers obtained by polymerization reaction using at least one, preferably two or more vinylic monomers as main raw material monomers, and preferred are cross-linkable polymers formed from a styrenic monomer(s).

The styrenic monomers include aromatic vinyl monomers, such as styrene, o-methylstyrene, m-methylstyrene, p-methylstyrene, 2,4-dimethylstyrene, ethylstyrene, p-t-butylstyrene, α-methylstyrene, α-methyl-p-methylstyrene, 1,1-diphenylethylene, p-(N,N-diethylaminoethyl)styrene, p-(N,N-diethylaminomethyl)styrene, vinylpyridine, and vinylnaphthalene.

In addition, a vinyl monomer copolymerizable with a styrenic monomer may be used in combination. Examples of the vinyl monomer include acrylic acid esters, methacrylic acid esters, acrylonitrile, maleic acid esters, vinyl acetate, olefins, and the like. In addition, to form a cross-linked structure, it is also possible to use a bifunctional monomer in combination. Examples thereof include divinylbenzene, alkylene glycol di(meth)acrylates, and the like.

The natural number n of the polymer compound represented by general formula (1) is smaller than the natural number of unit in the polymer backbone represented as Polymer. The natural number n represents a natural number attributed to the formation of a polymer containing a monomer a capable of binding to the linker L as at least one monomer.

The polymer compound represented by general formula (1) can be obtained by reacting the above-described polymer having a polymer backbone and a linker moiety (for example, a copolymer of a chloromethyl group-containing styrene and divinylbenzene) with imidazole in the presence of a base by using a suitable solvent at a reaction temperature of about 50 to 100° C.

The base may be an inorganic base, an organic base, or the like. Preferred inorganic bases include alkali metal hydroxides such as lithium hydroxide, sodium hydroxide, and potassium hydroxide; alkali metal carbonates such as lithium carbonate, sodium carbonate, and potassium carbonate; alkali metal hydrogen carbonates such as sodium hydrogen carbonate and potassium hydrogen carbonate; and metal hydrides such as sodium hydride. Preferred organic bases include alkali metal alkoxides such as lithium methoxide, sodium methoxides, potassium methoxide, sodium ethoxide, potassium ethoxide, sodium tert-butoxide, and potassium tert-butoxide; alkali metal carboxylates such as lithium acetate, sodium acetate, potassium acetate, and sodium propionate; amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, and N-methylmorpholine; and the like.

The solvent includes aliphatic hydrocarbons such as pentane, hexane, heptane, octane, decane, dodecane, undecane, cyclohexane, and decalin; aromatic hydrocarbons such as toluene, xylene, mesitylene, p-cymene, and diisopropylbenzene; halogenated aromatic hydrocarbons such as chlorobenzene and o-dichlorobenzene; ethers such as diethyl ether, diisopropyl ether, tert-butyl methyl ether, cyclopentyl methyl ether, dimethoxyethane, ethylene glycol diethyl ether, tetrahydrofuran, and 1,4-dioxane; ketones such as acetone, methyl ethyl ketone, methyl isobutyl ketone, and cyclohexanone; amides such as N,N-dimethylformamide and N,N-dimethylacetamide; nitriles such as acetonitrile, malononitrile, and benzonitrile; sulfoxides such as dimethyl sulfoxide; and the like. Each of these solvents may be used alone, or two or more thereof may be used, as appropriate, in combination. Specific examples of more preferred solvents include aliphatic hydrocarbons such as decane, dodecane, undecane, and decalin; aromatic hydrocarbons such as toluene, xylene, mesitylene, p-cymene, and diisopropylbenzene; ethers such as ethylene glycol diethyl ether, tetrahydrofuran, and 1,4-dioxane; amides such as N,N-dimethylformamide and N,N-dimethylacetamide; nitriles such as benzonitrile; sulfoxides such as dimethyl sulfoxide; and the like. More preferred solvents include ethers such as tetrahydrofuran and 1,4-dioxane. A further preferred solvent is tetrahydrofuran.

The amount of the solvent used is not particularly limited, as long as the reaction can proceed sufficiently. The amount of the solvent is selected, as appropriate, within the range of generally 1 to 500 times by volume, preferably 2 to 200 times by volume, and more preferably 2 to 100 times by volume relative to the above-described polymer having a polymer main chain and a linker moiety (for example, a copolymer of a chloromethyl group-containing styrene and divinylbenzene) and imidazole.

A method for synthesizing the polymer-supported zinc or cobalt of the present invention may be a method in which the polymer-supported metal is synthesized by reacting a zinc or cobalt compound represented by general formula (II):

$$MX_2 \cdot xH_2O \quad (II),$$

wherein X represents an optionally halogen atom-substituted alkanoyloxy group having 2 to 5 carbon atoms, a halogen atom, and a trifluoromethanesulfonyloxy group, x represents an integer, and M represents a zinc or cobalt atom, with a polymer compound represented by general formula (I):

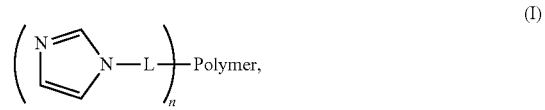

wherein Polymer represents a polymer backbone, L represents a linker moiety, and n represents a natural number.

In general formula (II), the halogen atom represented by X may be a chlorine atom, a bromine atom, or an iodine atom. Meanwhile, examples of the optionally halogen atom-substituted alkanoyloxy group having 2 to 5 carbon atoms represented by X include perfluoroalkanoyloxy groups such as a trichloroacetoxy group, a tribromoacetoxy group, a trifluoroacetoxy group, a pentafluoropropanoyloxy group, a heptafluorobutyryloxy group, and a heptafluoroisopropanoyloxy group. Among these, a preferred group may be a trifluoroacetoxy group. The zinc and cobalt compounds may be hydrates or anhydrates. In other words, when x in general formula (II) is 0, the zinc or cobalt compound is an anhydride, and when x represents an integer of 1 or greater, the zinc or cobalt compound is a hydrate. Since the zinc and cobalt compounds of general formula (II) are different in terms of stable crystalline hydrate, x often represents 1 to 10.

In addition, a method for synthesizing the Polymer-supported zinc of the present invention may be a method in which the Polymer-supported zinc is synthesized by reacting a zinc tetranuclear cluster represented by the following general formula (III):

$$Zn_4O(OCOR)_6(RCOOH)_n \quad (III),$$

wherein R represents an optionally halogen atom-substituted alkyl group having 1 to 4 carbon atoms, and n represents 0 to 1, with a polymer represented by general formula (I).

Examples of the optionally halogen atom-substituted alkyl group having 1 to 4 carbon atoms represented by R in formula (III) include perfluoroalkyl groups such as a trichloromethyl group, a tribromomethyl group, a trifluoromethyl group, a pentafluoroethyl group, a heptafluoropropyl group, and a heptafluoroisopropyl group. Of these groups, a preferred group may be a trifluoromethyl group.

As the solvent used for producing the polymer-supported metal of the present invention, any solvent can be used, as long as the solvent does not exert any influence on the formation of the polymer-supported metal of the present invention. In addition, a solvent capable of dissolving the metal inorganic salt or zinc carboxylate compound used as the raw material is preferable. For example, tetrahydrofuran (THF), benzene, toluene, xylene, hexane, heptane, octane, or the like can be used. Preferred are solvents such as toluene, xylene, and THF, and more preferred is THF.

The reaction temperature is preferably not lower than a temperature at which the metal inorganic salt or the metal carboxylate can be dissolved, and is from 30° C. to 250° C., and more preferably from 30° C. to 150° C.

The reaction time is not particularly limited, and the reaction can be conducted in generally approximately 1 to 45 hours, and preferably approximately 2 to 24 hours.

In most cases, the polymer-supported metal obtained during the reaction is insoluble in the solvent, and is precipitated. Hence, the polymer-supported metal can be obtained by filtration or the like after completion of the reaction.

The polymer-supported metal of the present invention obtained under the above-described conditions is stable in air, but is preferably handled in the presence of an inert gas. The inert gas is preferably nitrogen, argon, or the like.

When the polymer-supported metal of the present invention is used as a catalyst, the polymer-supported metal prepared in the presence of a suitable solvent (for example, THF) as described above in advance may be added as a catalyst to the reaction system, or the reaction may be conducted by adding the zinc or cobalt compound represented by general formula (II) or the zinc tetranuclear cluster represented by general formula (III), and the polymer compound represented by general formula (I), which are raw materials, to the reaction system (in situ method). In this case, the polymer-supported metal of the present invention is formed during the reaction or after the reaction.

When the polymer-supported metal of the present invention is used as a catalyst, a nitrogen-containing aromatic compound may be added in a catalytic amount. The addition of the nitrogen-containing aromatic compound enhances the activity, so that improvement in reaction time and conversion is observed. Nitrogen-containing compounds which may be added include pyridine, pyrimidine, pyrazine, pyridazine, 4-dimethylaminopyridine (DMAP), quinoline, N-methylimidazole (NMI), and the like. Preferred are DMAP and NMI, and further preferred is NMI.

The use of the polymer-supported metal of the present invention as a catalyst enables an alcoholic hydroxy group-selective acylation reaction or carbonate formation reaction, even in a case where an amino group, which is a nucleophilic functional group, and an alcoholic hydroxy group are simultaneously present in a reaction system.

The case where a nucleophilic functional group such as an amino group and an alcoholic hydroxy group are simultaneously present in a reaction system may refer to a case of a compound having an amino group and an alcoholic hydroxy group in a single molecule, or a case where an amino group and an alcoholic hydroxy group are present in different compounds. Compounds each having an amino group and an alcoholic hydroxy group in a single molecule include amino alcohols. Meanwhile, the case where the compound having an amino group and the compound having an alcoholic hydroxy group are different may be a case where an amine and an alcohol are simultaneously present in a reaction system.

The amino group may be a primary amino group or a secondary amino group, whereas the alcoholic hydroxy group may be any one of a primary hydroxy group, a secondary hydroxy group, and a tertiary hydroxy group. The amino alcohol is not particularly limited, as long as the compound has an amino group and an alcoholic hydroxy group. Examples thereof include linear, branched, cyclic, or fused-cyclic, aliphatic or aromatic amino alcohols and the like.

In general, an acylation reaction is conducted by treatment with an acyl chloride or an acid anhydride in the presence of a base such as pyridine or triethylamine. In contrast, the use of the polymer-supported metal of the present invention as a catalyst enables an acylation reaction based on a transesterification reaction between a carboxylic acid ester and a compound having an alcoholic hydroxy group under a neutral condition.

The use of the polymer-supported metal of the present invention as a catalyst enables a carbonate formation reaction based on a transesterification reaction between a carbonic acid ester and a compound having an alcoholic hydroxy group. The carbonic acid ester, which is a generic term for compounds in which one or two hydrogen atoms of the two hydrogen atoms of carbonic acid ($H_2CO_3$) are substituted with alkyl groups or aryl groups, used for carbonate formation reaction is preferably a dialkyl carbonate or diaryl carbonate, in which two hydrogen atoms are substituted, from the viewpoint of handling. Regarding specific examples, dimethyl carbonate, diethylmethyl carbonate, methyl ethyl carbonate, methyl phenyl carbonate, ethyl phenyl carbonate, or diphenyl carbonate is used. Of these carbonates, dimethyl carbonate is preferable.

The compound having an alcoholic hydroxy group may be a linear or cyclic, aliphatic hydrocarbon compound having one, two, or multiple hydroxy groups. In addition, for example, a cyclic carbonate compound can be obtained by reacting a compound having two or more hydroxy groups such as a diol compound with a carbonic acid ester by using the present catalyst.

The compound having an alcoholic hydroxy group may have an unsaturated bond(s), and may have a substituent(s). When the compound has a substituent(s), the substituent is not particularly limited, unless the substituent inhibits the reaction. Examples thereof include alkyl groups, alkenyl groups, alkynyl groups, aromatic groups, hydroxy groups, mercapto groups, amino groups, alkoxy groups, alkylthio groups, formyl groups, carboxyl groups, cyano groups, nitro groups, halogen atoms, hydrogen atoms, and the like, and different substituents may be present on these substituents.

Specific examples include the following compounds: alcohols having an aromatic substituent on an α-carbon bonded to a hydroxy group such as benzyl alcohol, 1-naphthylmethanol, 2-naphthylmethanol, 1-(1-naphthyl)ethan-1-ol, 1-(1-naphthyl)propan-1-ol, 1-(1-naphthyl)butan-1-ol, 9-fluorenylmethanol, tetralin-1-ol, 2-pyridinemethanol, and 3-pyridinemethanol; olefinic alcohols such as propen-3-ol, 1-buten-3-ol, and cyclohexen-3-ol; saccharides having an unsaturated bond in their molecules such as D-glucal, D-galactal, and L-rhamnal; and steroids having an unsaturated bond and a hydroxy group in their molecules such as 3-hydroxy-4-androstene-11,17-dione, 4-androstene-3,17-diol, and 5-estrene-3,17-diol.

In general, the above-described acylation reaction or carbonate formation reaction is carried out in a solvent. Examples of the solvent used include, but are not particularly limited to, aromatic hydrocarbon-based solvents such as toluene, xylene, and chlorobenzene; aliphatic hydrocarbon-based solvents such as hexane, heptane, and octane; ether-based solvents such as diethyl ether, diisopropyl ether, tert-butyl methyl ether, tetrahydrofuran, and 1,4-dioxane; amide-based solvents such as dimethylformamide (DMF), dimethylacetamide (DMAc), and N-methylpyrrolidone (NMP); dimethyl sulfoxide (DMSO); and the like.

The use of the polymer-supported metal of the present invention as a catalyst enables deacylation reaction of ester group-containing compounds. The ester group-containing compounds used for this reaction include carboxylic acid esters including aliphatic carboxylic acid esters and aromatic carboxylic acid esters, and the like. The esters may be those derived from monocarboxylic acids or polycarboxylic acids.

The ester group-containing compounds used for this reaction include alkyl esters such as methyl esters, ethyl esters, propyl esters, butyl esters, hexyl esters, and octyl esters; aryl esters such as phenyl ester, biphenyl ester, and naphthyl ester; aralkyl esters such as benzyl esters and 1-phenethyl esters of carboxylic acids described below, and the like. Preferred are methyl esters of the carboxylic acids described below.

Aliphatic carboxylic acids may be monocarboxylic or polycarboxylic acids having 2 to 30 carbon atoms, and specifically include acetic acid, propionic acid, butyric acid, valeric acid, hexanoic acid, heptanoic acid, octanoic acid, nonanoic acid, decanoic acid, dodecanoic acid, lauric acid, myristic acid, palmitic acid, stearic acid, oleic acid, oxalic acid, propanedicarboxylic acid, butanedicarboxylic acid, hexanedicarboxylic acid, sebacic acid, acrylic acid, and the like.

In addition, these aliphatic carboxylic acids may be substituted with alkyl groups, alkoxy groups, halogen atoms, amino groups, aryl groups, heteroaryl groups, aralkyl groups, silyloxy groups, and hydroxy groups as described above, and the like.

Aromatic carboxylic acids include benzoic acid, naphthalenecarboxylic acid, pyridinecarboxylic acid, quinolinecarboxylic acid, furancarboxylic acid, thiophenecarboxylic acid, and the like.

In addition, these aromatic carboxylic acids may be substituted with alkyl groups, alkoxy groups, halogen atoms, amino groups, aryl groups, heteroaryl groups, aralkyl groups, and hydroxy groups as described above, and the like. In general, this reaction is carried in a solvent, and the solvent may be an alcohol, specifically methanol, ethanol, propanol, isopropanol, 1-butanol, 2-butanol, or 3-butanol. Surprisingly, when the catalyst of the present invention is used, deacylation can also be conducted by using water. In addition, the reaction can be conducted in a mixture solvent of an organic solvent, including the above-described alcohols, and water.

The amount of the polymer-supported metal used as a catalyst for each of the reactions of the present invention is not particularly limited, and the ratio of zinc or cobalt atoms is generally 0.001 to 0.9 moles, more preferably 0.001 to 0.3 moles, further preferably 0.001 to 0.1 moles per mole of a raw material of each reaction.

The various reactions using the polymer-supported metal of the present invention as a catalyst can be conducted under the atmosphere, in air, or under an atmosphere of an inert gas such as nitrogen gas or argon gas.

The time of the various reactions using the polymer-supported metal of the present invention as a catalyst is not particularly limited, and the reactions can be conducted in generally approximately 1 to 45 hours, and preferably approximately 6 to 18 hours. The reaction temperature is not particularly limited, and the reactions are conducted at room temperature to approximately 180° C., preferably about 50 to 150° C., and more preferably about 80 to 150° C. These conditions are changed, as appropriate, depending on the type and the amount of the raw material used and the like.

The polymer-supported metal of the present invention is a heterogeneous catalyst in which zinc or cobalt is supported on a polymer, and hence can be easily recovered by filtration after the completion of each reaction. The recovered polymer-supported metal has the same structure as before the reaction, and undergoes no decrease in catalytic activity, making it possible to reuse the polymer-supported metal repeatedly.

Besides the filtration, when the substrate and the target product have low boiling points, the reaction liquid can also be directly concentrated after completion of the reaction as means for the recovery and reuse. In other words, the catalyst (polymer-supported metal) can be easily recovered and reused by removing the reaction solvent and the reaction raw material or the reaction product by distillation under reduced pressure or in an inert atmosphere at atmospheric pressure.

As described above, the polymer-supported metal of the present invention is extremely stable without undergoing decomposition or deactivation with the progress of the reaction as in the case of already reported catalysts, and further exhibits a high activity. In addition, it is characteristic that the polymer-supported metal undergoes a small amount of outflow (leaching) of the metal from the polymer-supported metal due to the reaction, and is a novel polymer-supported metal easy to recover and reuse. In addition, the polymer-supported metal is less susceptible to moisture than conventional zinc catalysts.

EXAMPLES

Hereinafter, the present invention will be described in detail based on Examples; however, the present invention is not limited thereto. Note that analytical instruments were as described below. In addition, all the operations in Examples were conducted under a nitrogen atmosphere.

Thermal analysis: EXSTAR 6000 TG/DTA 6200 (SII), measuring range: 30 to 600° C., heating speed: 6° C./min, measured amount: approximately 5 mg, sample pan: aluminum, atmosphere: nitrogen (10 mL/min) or in vacuum (2 Torr)

The metal content was determined by a titration method ("Kireto Tekitei (Chelate titration)," authored by Keihei Ueno (Nankodo Co., Ltd.)).

Chloromethyl polystyrene resin 1% DVB (divinylbenzene) cross-linked resin (Merrifield Resin cross-linked with 1% DVB (200-400 mesh)) (hereinafter, abbreviated as CH2-Polymer)

Zinc trifluoroacetate hydrate (manufactured by Alfa Aesar, zinc content: 21.24% (zinc titration measurement)) (hereinafter, abbreviated as $Zn(OAc^F)_2$)

Nuclear magnetic resonance spectra (NMR); Bruker Advanced III

High-resolution mass spectrometer (HRMS); ACQITY UPLC-LCT-Premier/XE, Bruker MicroTOF II (Reference Example 1) Synthesis of Imidazolyl Group-Containing Polymer (Hereinafter, im-CH2-Polymer)

For synthesis of an imidazolyl group-containing polymer, reference was made to Journal of Molecular Catalysis A: Chemical, 2012, 353-354, 178-184.

Under an Ar atmosphere, 3 equivalents of imidazole, 3.0 equivalents of sodium hydride, and CH2-Polymer were mixed together in 1,2-dimethoxyethane solvent, and heated at 60° C. for 3 days without adding a stirring bar. After the reaction, the excess sodium hydride was reacted with water in an ice bath, and then the reaction liquid was filtered under reduced pressure. The filtration residue was washed with water, diethyl ether, and dichloromethane to remove the excess imidazole, metal ions, and the like, and then dried in a vacuum to obtain the targeted im-CH2-Polymer. This was subjected to elemental analysis, and the imidazole content was calculated from the N value (first synthesis: 1.85 mmol/g, and second synthesis: 1.99 mmol/g). From these results, it was found that 90% of the chlorine atoms (2.4 mmol/g), which were reactive sites, contained in the raw material resin were substituted with imidazolyl groups.

(Reference Example 2) Synthesis of im-CH2-Polymer

In 10 mL of toluene, 5.3 g (78 mmol) of imidazole and 78 mg (0.47 mmol) of potassium iodide were dissolved, and heated with stirring under nitrogen at 40° C. To the reaction solution, a sodium methoxide methanol solution (MeONa, 4.2 g (78 mmol, 1 equivalent), 15 mL of methanol) was added dropwise. After that, CH2-Polymer and 30 mL of acetonitrile were added thereto. After heating with stirring at 65° C. for 12 hours, the mixture was cooled and filtered. The filtration residue was washed with methanol, and then dried under vacuum at 60° C.

The obtained polymer was subjected to simultaneous thermogravimetry/differential thermal analysis measurement (TG/DTA) in nitrogen gas at 10 mL/min. The imidazolyl group-containing polymer im-CH2-Polymer contained approximately 3% by weight of the solvents and the like, but no weight loss was observed up to about 340° C. It was found that decomposition of the polymer occurred at around 340° C.

(Example 1) Synthesis of Polymer-Supported Zinc Trifluoroacetate

To 1.00 g of im-CH2-Polymer synthesized in Reference Example 1, 0.30 g of $Zn(OAc^F)_2$ (zinc atoms: 63.3 mg) was added. In 10 mL of tetrahydrofuran, the mixture was refluxed under nitrogen for 5 hours, and then cooled to room temperature and filtered. The filtration residue was washed three times with 10 mL of tetrahydrofuran, and further with 30 mL of heptane. The obtained solid substance was placed in a Schlenk tube, and dried under heating at 65° C. in a vacuum to obtain 1.16 g of the target polymer.

The reaction solution filtered as described above and the washing liquid were evaporated under reduced pressure, and then the zinc content in the solution was determined by the above-described titration method. It was found that 1.4 mg of zinc atoms were contained. From the above-described result, 61.9 mg of zinc atoms were adsorbed on the polymer, and the polymer contained 53.4 mg/g (0.83 mmol/g) of zinc atoms.

The polymer-supported zinc was subjected to simultaneous thermogravimetry/differential thermal analysis measurement (TG/DTA) in nitrogen gas at 10 mL/min (FIG. 1), and a weight loss (Δ7.2%) was observed at around 210° C., before the decomposition of the polymer occurred at around 340° C.

The zinc trifluoroacetate hydrate, which was the raw material, was subjected to TG/DTA measurement, and a weight loss was observed at a ratio equivalent to trifluoroacetic acid groups at the same temperature. It was found that the weight loss at around 210° C. was due to a desorption phenomenon of trifluoroacetic acid groups.

Examples 2 to 6

Polymer-supported zinc trifluoroacetate were synthesized under various conditions in the same manner as in Example 1. Table 1 below shows the results of Examples 1 to 6.

TABLE 1

| Example | Im-CH2-Polymer (g) | $Zn(OAc^F)_2$ (g) | Zinc Atoms (mmol) | Solvent | Polymer-supported zinc (g) |
|---|---|---|---|---|---|
| 1 | 1.00 | 0.30 | 0.97 | THF | 1.16 |
| 2 | 0.50 | 0.49 | 1.58 | THF | 0.58 |
| 3 | 1.00 | 0.10 | 0.33 | THF | 1.02 |
| 4 | 0.99 | 0.30 | 0.97 | i-PrOH | 1.28 |
| 5 | 1.00 | 0.31 | 0.99 | n-BuOH | 1.27 |
| 6 | 0.99 | 0.03 | 0.11 | THF | 0.97 |

(Examples 7 to 12) Synthesis of Polymer-Supported Other Metal Inorganic Salt

Polymer-supported other metal inorganic salt were synthesized. To im-CH2-Polymer synthesized in Reference Example 1, each metal inorganic salt was added, and the mixture was refluxed in a reaction solvent under nitrogen for 5 hours, and then cooled to room temperature and filtered. The filtration residue was washed three times with tetrahydrofuran, and further once with heptane. The obtained solid substance was placed in a Schlenk tube, and dried under heating at 65° C. in a vacuum to obtain polymer-supported the metal inorganic salt. Table 2 below shows the results of the synthesis of Examples 7 to 12.

TABLE 2

| Example | CH2-Polymer (g) | Metal Salt and Amount used (g) | Metal Atoms (mmol) | Solvent | Polymer-supported metal (g) |
|---|---|---|---|---|---|
| 7 | 5.65 | $CF_3CO_2Na$ (0.950) + $ZnCl_2$ (0.488) | 3.58 | THF | 6.76 |
| 8 | 0.35 | $ZnI_2$ (0.08) | 0.80 | EtOH | 0.35 |
| 9 | 1.01 | $Zn(CH_3CO_3)_2$ (0.17) | 0.94 | THF | 1.15 |
| 10 | 0.30 | $Zn(CF_3SO_3)_2$ (0.08) | 0.22 | THF | 0.33 |
| 11 | 0.65 | $CoCl_2, 6H_2O$ (0.10) + $CF_3CO_2Na$ (0.12) | 0.44 | THF | 0.76 |
| 12 | 0.29 | $CoCl_2, 6H_2O$ (0.05) | 0.19 | THF | 0.29 |

Figure 2:
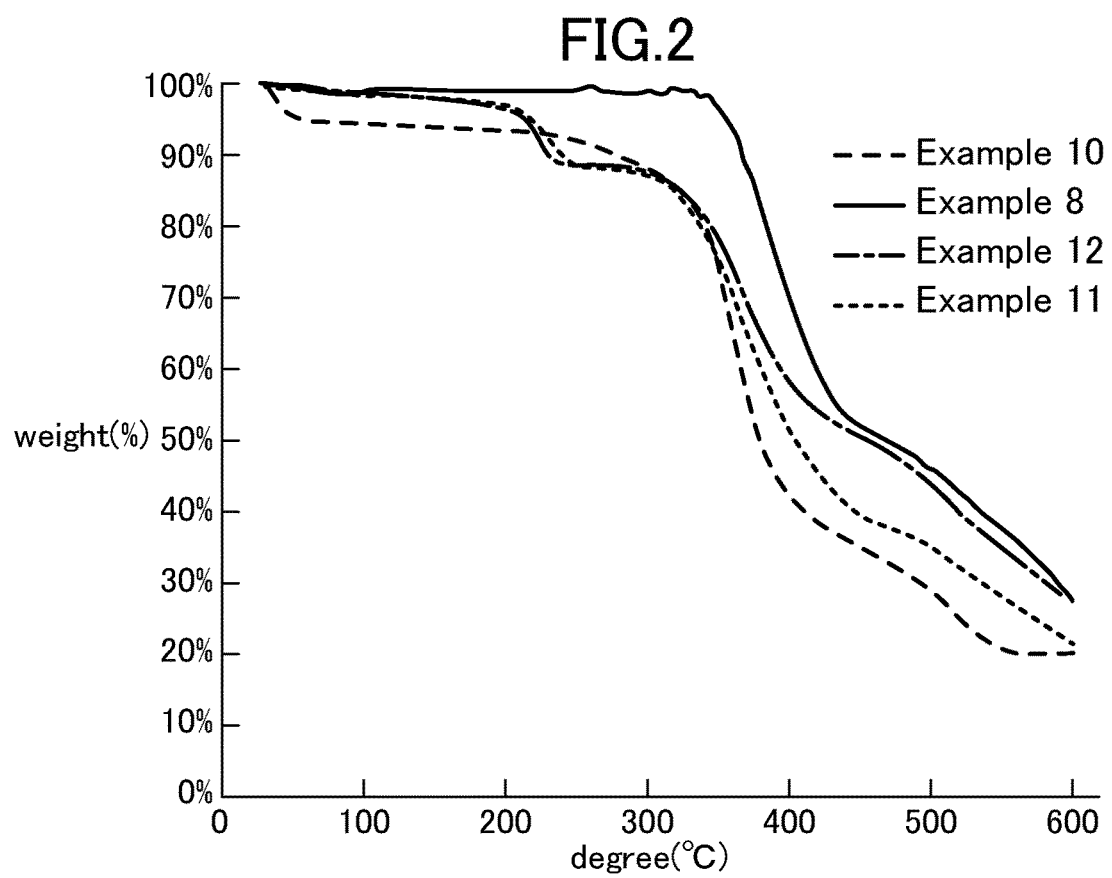
FIG. 2 is a graph showing the results obtained when polymer-supported metal prepared in Examples 8, 10, 11, and 12 were subjected to simultaneous thermogravimetry/differential thermal analysis measurement (TG/DTA) in nitrogen gas at 10 mL/min.

The obtained polymer-supported metal was subjected to simultaneous thermogravimetry/differential thermal analysis measurement (TG/DTA) in nitrogen gas at 10 mL/min (FIG. 2). For each of the polymer-supported zinc trifluoromethanesulfonate (Example 10) and the Polymer-supported zinc iodide (Example 8), no weight change was observed before the decomposition of the polymer. On the other hand, for the cobalt chloride and polymer-supported cobalt acetate (Example 11) and the polymer-supported cobalt chloride (Example 12), a weight loss associated with the desorption of their respective anions was observed before the decomposition of the polymer, because the molecular weight of the anions was smaller than that of trifluoromethanesulfonate or iodine ions.

(Example 13) Transesterification Reaction

To 1 equivalent of methyl benzoate and 1.2 equivalents of benzyl alcohol, 5% by mole (in terms of zinc atoms) of zinc trifluoroacetate and im-CH2-Polymer synthesized in Reference Example 1 at various ratios relative to the zinc atoms were added, and transesterification reaction was conducted by reflux in toluene solvent for 6 hours. Table 3 below shows the results of the conversion of methyl benzoate measured by gas chromatography (GC). It was found that the conversion was high, when the ratio (im/Zn) of the imidazolyl groups in the polymer-supported relative to the zinc atoms was 4 or higher.

TABLE 3

| im/Zn | Zn (wt %) | Conversion (%) |
|---|---|---|
| 0.5 | 19.9% | 23 |
| 1 | 11.0% | 21 |
| 2 | 5.8% | 36 |
| 4 | 3.0% | 86 |
| 8 | 1.5% | 92 |

(Example 14) Comparison of Catalytic Activities with Various Imidazolyl Group Contents Table 4 shows the results of a comparison of the effect of adding zinc trifluoroacetate by using three types of im-CH2-Polymer having different imidazole-supporting amounts. To 1 equivalent of methyl benzoate and 1.2 equivalents of benzyl alcohol, 5% by mole (in terms of zinc atoms) of zinc trifluoroacetate and im-CH2-Polymer synthesized in Reference Example 1 at various ratio relative to the zinc atoms were added, and transesterification reaction was conducted by reflux in toluene solvent (0.5 M) for 2 hours. Table 4 below shows the results of the yield of methyl benzoate measured by gas chromatography (GC). It was found that the conversion was high, when the ratio (im/Zn) of the imidazolyl groups in the imidazolyl-supporting resin relative to the zinc atoms was 4 or higher. It was found that im-CH2-Polymer containing imidazolyl groups at a higher ratio of 4.98 mmol/g had lower activity than im-CH2-Polymers having imidazolyl group contents of 1.25 mmol/g and 1.85 mmol/g.

TABLE 4

| im-CH2-Polymer | Zinc Catalyst | Yield (%) |
|---|---|---|
| Im = 1.25 mmol/g | $Zn(OAc^F)_2$ + im-CH2-Polymer (Im/Zn) = 2/1 | 7 |
| | $Zn(OAc^F)_2$ + im-CH2-Polymer (Im/Zn) = 4/1 | 66 |
| Im = 1.85 mmol/g | $Zn(OAc^F)_2$ + im-CH2-Polymer (Im/Zn) = 2/1 | 4 |
| | $Zn(OAc^F)_2$ + im-CH2-Polymer (Im/Zn) = 4/1 | 63 |
| | $Zn(OAc^F)_2$ + im-CH2-Polymer (Im/Zn) = 8/1 | 72 |
| Im = 4.98 mmol/g | $Zn(OAc^F)_2$ + im-CH2-Polymer (Im/Zn) = 2/1 | 6 |
| | $Zn(OAc^F)_2$ + im-CH2-Polymer (Im/Zn) = 4/1 | trace |

(Example 15) Acetylation with Ethyl Acetate

In ethyl acetate (0.50 M), 0.50 mmol of benzyl alcohol and the polymer-supported zinc synthesized in Example 1 (5% by mole in terms of zinc atoms) were refluxed for 1 hour. The reaction liquid was filtered and the filtrate was analyzed. The benzyl acetate formation from benzyl alcohol proceeded with a conversion of 99% or higher. The polymer-supported zinc used as the catalyst was recovered as a filtration residue.

(Example 16) Methoxycarbonylation with Dimethyl Carbonate

In dimethyl carbonate (0.50 M), 0.50 mmol of benzyl alcohol and the polymer-supported zinc synthesized in Example 1 (5% by mole in terms of zinc atoms) were refluxed for 30 minutes. Methoxycarbonylation of benzyl alcohol proceeded with a conversion of 99% or higher.

1H NMR (500 MHz, CDCl3, 27° C.): δ 7.40-7.33 m, 5H, Ph), 5.17 (s, 2H, CH2), 3.80 (s, 3H, CH3); 13C NMR (125 MHz, CDCl3, 27° C.) δ 155.7, 135.3, 128.6, 128.5, 128.3, 69.7, 54.9

(Example 17) Deacetylation with Methanol

In methanol (0.50M), 0.50 mmol of benzyl acetate and the polymer-supported zinc synthesized in Example 1 (5% by mole in terms of zinc atoms) were refluxed for 2 hours. Deacetylation of benzyl acetate proceeded with a conversion of 78%.

(Example 18) Synthesis of Polymer-Supported Zinc after Transesterification

To 0.99 g of geraniol, 88.0 mg of $Zn_4(OCOCF_3)_6O$ (zinc content: 24% by weight (zinc titration measurement), equivalent to 21.1 mg of zinc atoms, 5.03% by mole) was added, and the mixture was refluxed for 1 hour by using butyl acetate as a solvent. The conversion of geraniol based on GC measurement was 90.2%. Subsequently, 204.4 mg of im-CH2-Polymer synthesized in Reference Example 1 was added, and then the mixture was stirred at the same temperature for further 1 hour. After cooling to room temperature, filtration was carried out. In the filtrate containing the reaction product, geranyl acetate, 3.2 mg of zinc atoms were detected by the zinc titration measurement method. Since the amount of zinc atoms used under the above-described reaction conditions was 21.0 mg, it was found that 17.9 mg of the zinc atoms were adsorbed on the polymer. In other words, 87.6 mg of zinc was adsorbed per gram of im-CH2-Polymer.

(Example 19) Recycle Experiment

Transesterification reaction was conducted by using the polymer-supported zinc recovered by filtration in Example 15. To 1.00 g (6.48 mmol) of geraniol and 204.0 mg of the polymer-supported zinc obtained by filtration in Example 15, 5 mL of 1-butanol was added, followed by stirring at reflux temperature. Based on a GC analysis, the conversion of geraniol was 87.6% at a reaction time of 8 hours. After cooling, the reaction solution was filtered to obtain the reaction product, geranyl acetate. The zinc content in this filtrate was determined by the titration method. 0.196 mg of zinc was detected. The catalyst was recovered by filtration. In the same manner by using the polymer-supported zinc obtained by filtration as described above, 5 mL of 1-butanol was added to 0.99 g (6.41 mmol) of geraniol and 196.29 mg of the polymer-supported zinc, followed by stirring at reflux temperature. Based on a GC analysis, the conversion of geraniol was 79.8% at a reaction time of 8 hours. After cooling, the reaction solution was filtered to obtain the reaction product, geranyl acetate. The zinc content in this filtrate was determined by the titration method. 0.16 mg of zinc was detected. It was thus found that the polymer-supported zinc of the present invention had a catalytic activity for transesterification, further had reactivity even when recycled twice or three times, and underwent a small amount of outflow (leaching) of zinc.

(Example 20) Synthesis of Polymer-Supported Zinc at Transesterification

To 1.0 g of geraniol, 108.6 mg (0.353 mmol) of $Zn(OAc^F)_2$ and further 204 mg of im-CH2-Polymer synthesized in Reference Example 1 were added, and the reaction was allowed to proceed in 5 mL of butyl acetate at reflux temperature for 5 hours. Based on GC measurement, the conversion of geraniol was 78.3%. After cooling to room temperature, filtration was carried out. The catalyst was recovered as the filtration residue.

In the filtrate, 4.53 mg of zinc atoms was detected by the zinc titration measurement method. Since the amount of zinc atoms of the catalyst used in the above-described reaction was 23.1 mg, it was found that 18.5 mg of zinc atoms were adsorbed on the polymer. In other words, 87.6 mg of zinc was adsorbed per gram of im-CH2-Polymer. After the adsorption, the polymer was dried under reduced pressure, and then subjected to TGA thermal analysis measurement. Similar analysis results were obtained to those of the catalyst at the synthesis of the polymer-supported zinc complex of Example 1.

Comparative Example 1

To 1.0 g of geraniol, 214.8 mg of im-Ch2-Polymer synthesized in Reference Example 1 was added, and the reaction was allowed to proceed in 5 mL of butyl acetate at reflux temperature for 8 hours. However, almost no transesterification reaction occurred. This showed that im-CH2-Polymer synthesized in Reference Example 2 had no transesterification activity.

(Example 21) Transesterification Reaction

Figure 3:
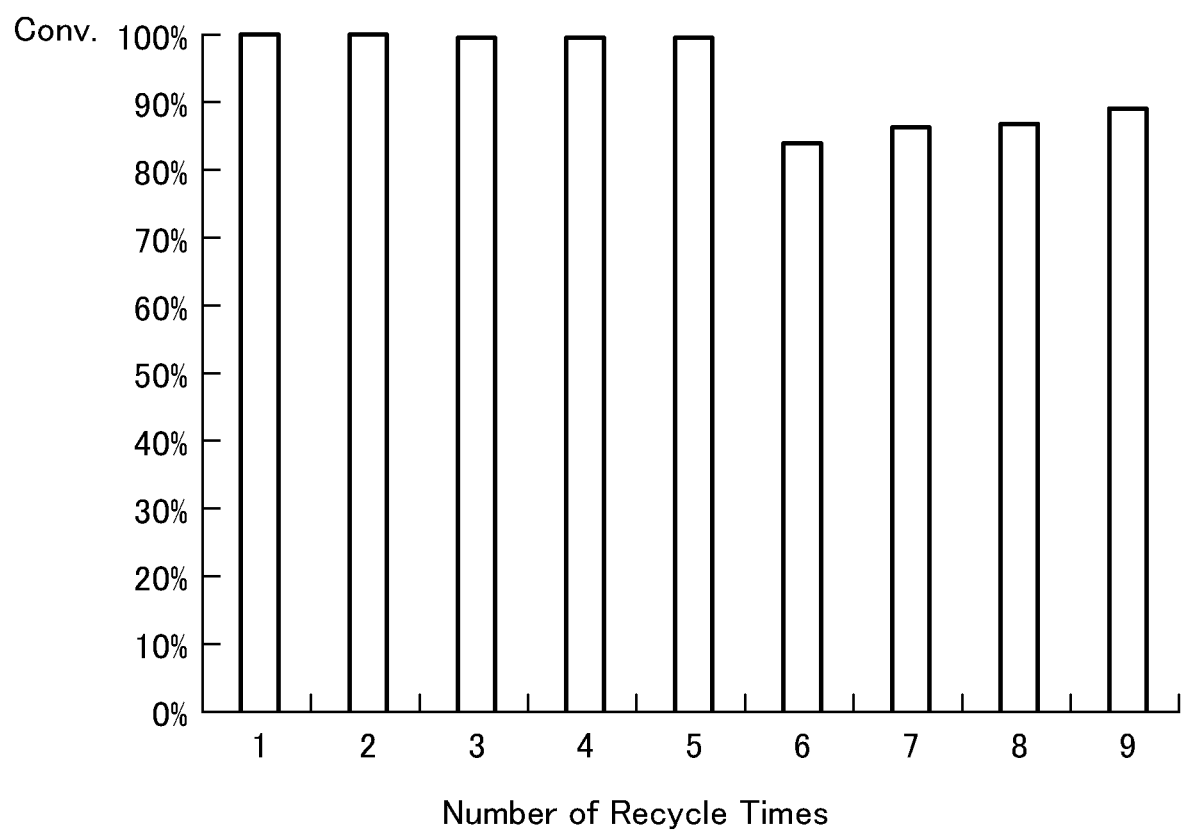
FIG. 3 shows the GC measurement results of conversions in reactions in recycle experiments conducted in Example 21.

To 0.2 g of methyl benzoate, 0.202 g (1.2 equivalents) of cyclohexylmethanol, and 4 mL of chlorobenzene, the polymer-supported zinc synthesized in Example 1 (4% by mole) was added as a catalyst. After reflux in air for 5 hours, the conversion (Conv.) was measured by GC. The conversion of methyl benzoate was 99.8% or higher. After the reaction, the cooled reaction solution was filtered, and the catalyst, which was the filtration residue, was washed with heptane, and dried at room temperature in a vacuum. A recycle experiment was conducted by using the recovered zinc catalyst under the same reaction conditions as those described above, and the conversion of the reaction was measured by GC (FIG. 3). Even when the recycle reaction was conducted 9 times, the conversion was 80% or higher as shown in FIG. 3. This showed that the supported zinc hardly underwent outflow due to the reaction, and the reactivity was retained. It is conceivable that the present catalyst is useful for flow reaction and the like.

(Example 22) Transesterification Reaction

A comparison was made by adding various polymer-supported zincs as catalysts to 0.2 g of methyl benzoate, 0.202 g (1.2 equivalents) of cyclohexylmethanol, and 4 mL of chlorobenzene. After reflux in air for 5 hours, the change in conversion was determined by GC. Consequently, the catalyst having a trifluoroacetic acid group exhibited the highest activity. The catalysts having halogen atoms or triflate groups had lower activity than the catalyst having trifluoroacetic acid.

In addition, recycle experiments of the above-described transesterification reaction were conducted by using the polymer-supported cobalt trifluoroacetate having the highest catalytic activity. Even when the polymer was used three times for the reaction, the conversion was 90% or higher. By the metal titration measurement, it was also found that the amount of the cobalt outflow (leaching) in the reaction liquid was small.

(Example 23) Transesterification by In-Situ Method

Transesterification reaction was conducted by refluxing 410 mg of im-CH2-Polymer synthesized in Reference Example 2, 19.4 mg (1.0% by mole) of $Zn_4(OCOCF_3)_6O$, 20.1 mg (3.4 mmol) of N-methylimidazole, and 0.2 g of L-menthol in butyl acetate under nitrogen for 23 hours. The conversion of L-menthol was 98.4%, as measured by GC. After the reaction, the obtained ester compound was successfully recovered only by addition of heptane, filtration, and solvent evaporation (GC purity: 96.0%, the raw material 1-menthol accounted for 4%). It was shown that the addition of N-methylimidazole enhanced the catalytic activity.

The zinc content due to the outflow from the polymer-supported zinc catalyst into the reaction liquid during the reaction was analyzed by titration measurement of the filtrate. The zinc content was not higher than the analytical limit (1 ppm or less). It was confirmed that zinc atoms were hardly removed from the polymer-supported zinc hardly during the reaction.

(Example 24) Transesterification by In-Situ Method

In butyl acetate, 210 mg of im-CH2-Polymer synthesized in Reference Example 2, 6.7 mg (0.34% by mole) of $Zn_4(OCOCF_3)_6O$, 3.1 mg (0.52 mmol) of N-methylimidazole, and 0.2 g of L-menthol were refluxed under nitrogen for 34 hours. The conversion of L-menthol was 93.8%, as measured by GC.

After the reaction, the reaction liquid was filtered without adding heptane to remove the polymer-supported zinc catalyst. The zinc content in the reaction product in the case where the filtration was conducted without adding heptane, which was a poor solvent, was analyzed by the zinc titration measurement. The zinc content was 30 ppm, and this result also revealed that a small amount of zinc metal was removed by the reaction.

(Example 25) Repeated Reaction

The acetylation reaction was again conducted by using the polymer-supported zinc catalyst recovered by filtration after the reaction was conducted in Example 24 described above and by using the same substrate as in Example 24 (reaction time: 19 hours). The conversion of L-menthol was 75.7%, as measured by GC.

(Example 26) Transesterification by In-Situ Method

A transesterification reaction was conducted by adding 77.1 mg of im-CH2-Polymer synthesized in Reference Example 2, 49.0 mg of $Zn_4 (OCOCF_3)_6O$, and 24.7 mg of N-methylimidazole. The conversion was 99.8% at a reaction time of 9 hours.

(Example 27) Transesterification by In-Situ Method

In butyl acetate, 210 mg of im-CH2-Polymer synthesized in Reference Example 2, 19.4 mg (1% by mole) of $Zn_4 (OCOCF_3)_6O$, 20.1 mg (3.4 mmol %) of N-methylimidazole, and 0.2 g of L-menthol were refluxed under nitrogen for 23 hours. The conversion of L-menthol was 98.4%, as measured by GC. After the reaction, 5 mL of heptane was added, followed by filtration and solvent evaporation to obtain the product. Based on the results of $^1$H-NMR measurement, the purity was 96.0%. No zinc was contained in the reaction liquid, which was the filtrate. This showed that no outflow of zinc atoms took place, even though the conversion was high.

From the above-described results, it has been found that, in order to completely support zinc atoms in the case (in situ method) were the complex is synthesized in the system by using im-CH2-Polymer, a relatively large amount of im-CH2-Polymer has to be added. It was found that, by conducting the reaction with a suitable ratio, the reaction was successfully completed with a high conversion and without outflow of zinc.

(Example 28) Deacetylation with Methanol

By using 0.2 g of each of cinnamyl acetate and geranyl acetate, deacetylation reactions were conducted at reflux temperature for a reaction time of 6 hours in methanol solvent (0.50 M) to which the polymer-supported zinc trifluoroacetate synthesized in Example 1 (ratio of catalyst: 5% by mole in terms of zinc) was added. The target products were obtained from both compounds only by filtration and solvent evaporation (the yield was 99% or higher for each compound).

(Comparative Example 2) Deacetylation with Methanol

To 0.50 mmol of cinnamyl acetate, 1% by mole of im-CH2-Polymer synthesized in Reference Example 2 was added, and the reaction was allowed to proceed in methanol solvent (0.50 M) at reflux temperature for a reaction time of 6 hours. However, no reaction took place. From this, it has been found that im-CH2-Polymer synthesized in Reference Example 2 does not have a transesterification activity.

(Example 29) Deacetylation with Methanol Using 4-Acetoxystyrene

The reaction was conducted by using the trifluoroacetic acid-supporting polymer synthesized in Example 1 at a ratio of 1.0% by mole relative to 4-acetoxystyrene, and 4-vinylphenol was obtained at a reaction time of 6 hours (conversion: 95.3%). Moreover, addition of 4.0% by mole of N-methylimidazole (NMI) under the above-described reaction conditions accelerated the reaction (conversion: 97.8%, reaction time: 5 hours).

(Example 30) Deacetylation Using 4-Acetoxystyrene in Water

Hydrolysis was conducted by using 0.20 g (1.04 mmol) of 4-acetoxystyrene, 52.7 mg of the polymer supported zinc trifluoroacetate synthesized in Example 1, and 4 mL of water as a solvent (reaction time: 9 hours, conversion: 43.7%). Also from the fact that the conversion showed a proportional relationship to the reaction time, it has been found that the zinc catalyst causes the reaction to proceed without losing its activity. It has been found that the catalyst of the present invention causes the reaction to proceed without losing its activity in contrast to conventional zinc catalysts which lose their activity because of decomposition in water.

(Example 31) Deacetylation in Methanol Solvent

A methanolysis reaction was examined by using 0.2 g (0.88 mmol) of lauryl acetate, 1% by mole of the catalyst (the polymer-supported zinc synthesized in Example 1) in which zinc trifluoroacetate was supported on im-CH2-Polymer synthesized in Reference Example 2, and 4 mL of methanol (reaction time: 15 hours, 68.7% conversion). Similarly, improvement in conversion was observed owing to an effect of the addition of NMI (4% by mole) (reaction time: 7 hours, conversion: 91.4%).

(Example 32) Methoxycarbonylation in Dimethyl Carbonate Solvent

Methoxycarbonylation reactions were examined in dimethyl carbonate (0.50 M) by using 0.2 g of each of cinnamyl alcohol and geraniol as a substrate, and using 5% by mole of a catalyst in which zinc trifluoroacetate was supported on the polymer-supported zinc synthesized in Example 1. At a reaction time of 3 hours, cinnamyl methyl carbonate was obtained in a yield of 99% or higher, and geranyl methyl carbonate was obtained in a yield of 97%. The target products were obtained only by filtration and solvent evaporation.

Cinnamyl methyl carbonate; 1H NMR (500 MHz, CDCl3, 27° C.): δ 7.40-7.39 (m, 2H, Ph), 7.28-7.25 (m, 1H, Ph), 6.68 (d, 1H, J=16.0, PhCH), 6.30 (dt, 1H, J=16.0, 6.5, PhCHCH), 4.79 (m, 2H, CH2), 3.81 (s, 3H, CH3); 13C NMR (125 MHz, CDCl3, 27° C.) δ 155.7, 135.3, 128.6, 128.5, 128.3, 69.7, 54.9

Geranyl methyl carbonate; 1H NMR (500 MHz, CDCl3, 27° C.): δ 5.37 (m, 1H, OCH2CH), 5.07 (m, 1H, CH3CH), 4.66 (d, 2H, J=7.0, OCH2), 3.78 (s, 3H, OCH); 13C NMR (125 MHz, CDCl3, 27° C.): δ 155.9, 143.2, 131.9, 123.7, 117.7, 64.7, 54.6, 39.5, 26.2, 25.7, 17.7, 16.5

(Example 33) Cyclic Carbonate Formation from 1,2-Diol, and Carbonate Decomposition In dimethyl carbonate (0.5 M), 0.2 g of 1-phenoxyethane-1,2-diol and 5% by mole of the trifluoroacetic acid-supporting polymer synthesized in Example 1 were refluxed for 3 hours, and 4-phenoxy-1,3-dioxolan-2-one was obtained in an isolated yield of 95%.

1H NMR (500 MHz, CDCl3, 27° C.): δ 7.31 (t, 2H, J=7.5, Ph), 7.02 (t, 1H, J=7.5, Ph), 6.91 (d, 2H, J=8.0, Ph), 5.03 (m, 1H, OCH), 4.62 ((t, 1H, J=8.5, OCH), 4.55 (t, 1H, J=8.5, OCH), 4.24 (m, 1H, OCH), 4.17 (m, 1H, OCH); 13C NMR (125 MHz, CDCl3, 27° C.): δ 157.8, 154.7, 129.7, 122.0, 114.6, 74.1

In addition, 0.2 g of 4-phenoxy-1,3-dioxolan-2-one and 5% by mole of the trifluoroacetic acid-supporting polymer synthesized in Example 1 were added to methanol solvent (0.5 M), and refluxed for 6 hours to obtain 1-phenoxyethane-1,2-diol in an isolated yield of 97%. In both reactions, the target products were obtained only by filtration and solvent evaporation.

(Example 34) Methoxycarbonylation in Dimethyl Carbonate Solvent

Methoxycarbonylation was conducted by adding 5% by mole of various polymer-supported zincs as catalysts to propargyl alcohol (0.1 g, 1.78 mmol) in dimethyl carbonate solvent (4 mL), followed by reflux in air. Table 5 shows the results.

TABLE 5

| Catalyst | Zn/Substrate | Conversion |
| --- | --- | --- |
| PS—CH2-imZn(OAc$^F$)$_2$ | 1.2% | 99.91% |
| PS—CH2-imCoOCOCF$_3$ | 1.4% | 96.53% |
| PS—CH2-imCoCl$_2$ | 1.5% | 90.37% |

After the reaction, the catalyst was filtered, the solvent was evaporated, and H-NMR measurement was conducted. However, no polymer was observed.

(Example 35) Functional Group-Selective Esterification

To 0.8 mL of toluene solution of 0.6 mmol of 6-amino-1-hexanol and 0.7 mmol of methyl benzoate, 5% by mole of the zinc trifluoroacetate-supporting polymer synthesized in Example 1 was added, followed by reflux for 5 hours. After the reaction, the catalyst was filtered, and then the solvent was evaporated. After methylene chloride was added, di-tert-butyl dicarbonate (0.30 mL, 1.3 mmol) and triethylamine (0.18 ml, 1.3 mmol) were added, and then the reaction was allowed to proceed in at room temperature for 1 hour. After the reaction, the organic layer was washed twice with 10 ml of distilled water, followed by liquid-liquid separation. Then, the obtained organic layer was concentrated, and then subjected to flash column chromatography to obtain 0.46 mmol of 6-((tert-butoxycarbonyl)amino)hexyl benzoate. Yield: 91%. Hydroxy group/amino group selectivity=>20/1

1H NMR (500 MHz, CDCl3, 27° C.): δ 8.04 (m, 2H, Ph), 7.55 (m, 1H, Ph), 7.43 (m, 2H, Ph), 4.50 (br, 1H, CONH), 4.32 (t, 2H, J=6.5, OCH2), 3.12 (br, 2H, NCH2), 1.78 (m, 2H, CH2), 1.53-1.37 (m, 15H, CH2, Boc); 13C NMR (125 MHz, CDCl3, 27° C.): δ 166.7, 156.0, 132.8, 130.5, 129.5, 128.3, 79.1, 64.9, 40.5, 30.0, 28.7, 28.4, 26.5, 25.8

(Example 36) Chemoselective Methoxycarbonylation in Dimethyl Carbonate Solvent

A methoxycarbonylation reaction was conducted by refluxing equal amounts of cyclohexyl alcohol and cyclohexylamine in 4 mL of dimethyl carbonate solvent in air for 5 hours with 5.5% by mole of a zinc catalyst added thereto. Almost only the reaction of the alcohol occurred (conversion: 99.9% or higher, selectivity: 96%).

(Example 37) Acetylation in Ethyl Acetate Solvent

Reactions were conducted by using 5% by mole of the trifluoroacetic acid-supporting polymer synthesized in Example 1 in ethyl acetate (AcOEt) solvent (0.5 M) at reflux temperature. The following acetylated products were obtained from alcohols in high yields.

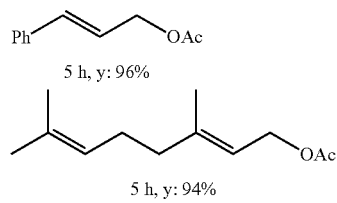

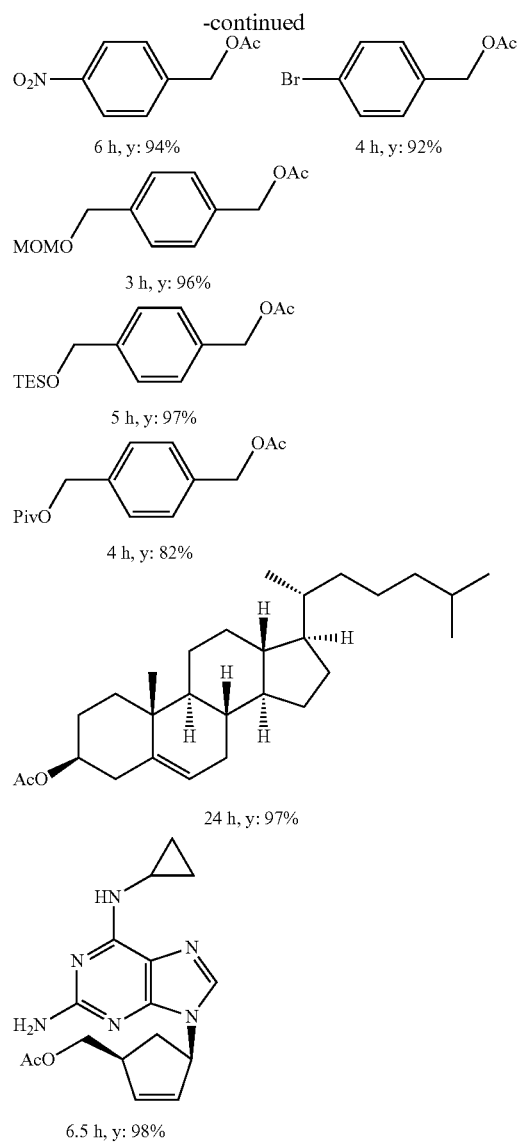

4-Nitrobenzyl acetate; 1H NMR (500 MHz, CDCl3, 27° C.): δ 8.23 (dd, 2H, J=7.0, 2.0, Ar), 7.52 (d, 2H, J=9.0, Ar), 5.20 (s, 2H, ArCH2), 2.15 (s, 3H, CH3); 13C NMR (125 MHz, CDCl3, 27° C.): δ 170.5, 147.7, 143.2, 128.4, 123.8

4-Bromobenzyl acetate; 1H NMR (500 MHz, CDCl3, 27° C.): δ 7.48 (d, 2H, J=8.5, Ar), 7.23 (d, 2H, J=8.5, Ar), 5.05 (s, 2H, ArCH2), 2.10 (s, 3H, CH3); 13C NMR (125 MHz, CDCl3, 27° C.): δ 170.7, 135.0, 131.7, 129.9, 122.3, 65.5, 20.9

4-((Methoxymethoxy)methyl)benzyl acetate; 1H NMR (500 MHz, CDCl3, 27° C.): δ 7.35 (m, 4H, Ar), 5.10 (s, 2H, OCH2), 4.70 (s, 2H, OCH2), 4.59 (s, 2H, OCH2), 3.41 (s, 3H, CH3), 2.09 (s, 3H, CH3); 13C NMR (125 MHz, CDCl3, 27° C.): δ 170.8, 138.0, 135.4, 128.4, 128.0, 95.7, 68.8, 66.0, 55.4, 21.0; HRMS (EI) m/z cald. for C12H15O4 223.0976 found 223.0985.

4-(((Triethylsilyl)oxy)methyl)benzyl acetate; 1H NMR (500 MHz, CDCl3, 27° C.): δ 7.32 (m, 4H, Ar), 5.09 (s, 2H, OCH2), 4.73 (s, 2H, OCH2), 2.09 (s, 3H, CH3), 0.98 (t, 9H, J=8.0, SiCH2CH3), 0.65 (q, 6H, J=8.0, SiCH2); 13C NMR (125 MHz, CDCl3, 27° C.): δ 170.9, 141.6, 128.9, 126.3, 66.2, 64.4, 21.0, 6.8, 4.5

4-(Acetoxymethyl)benzyl pivalate; 1H NMR (500 MHz, CDCl3, 27° C.): δ 7.36-7.26 (m, 4H, Ar), 5.10 (s, 4H, OCH2), 2.10 (s, 3H, CH3), 1.23 (s, 9H, Piv); 13C NMR (125 MHz, CDCl3, 27° C.) δ 178.3, 170.8, 136.6, 135.7, 128.4, 127.9, 66.0, 65.7, 38.8, 27.2, 21.0

Cholesteryl acetate; 1H NMR (500 MHz, CDCl3, 27° C.): δ 5.38 (d, 1H, J=5.0, CCH), 4.61 (m, 1H, OCH), 2.32 (m, 2H), 2.03-1.95 (m, 5H), 1.87-1.84 (m, 3H), 1.60-0.92 (m, 27H), 0.87 (m, 6H, CH3); 13C NMR (125 MHz, CDCl3, 27° C.): δ 170.5, 139.7, 122.7, 74.0, 56.7, 56.1, 50.0, 42.3, 39.7, 39.5, 38.1, 37.0, 36.6, 36.2, 35.8, 31.9, 28.2, 27.8, 24.3, 23.8, 22.8, 22.6, 21.4, 21.0, 19.3, 18.7, 11.9

((1S,4R)-4-(2-Amino-6-(cyclopropylamino)-9H-purin-9-yl)cyclopent-2-en-1-yl)methyl acetate; 1H NMR (500 MHz, CDCl3, 27° C.) δ 7.51 (s, 1H, CCH), 5.90 (m, 1H, CCH), 5.66 (br, 1H, ArNH), 5.55 (m, 1H, NCH), 4.79 (br, 2H, ArNH2), 4.19-4.10 (m, 2H, cyclopropyl), 0.61 (m, 2H, cyclopropyl); 13C NMR (125 MHz, CDCl3, 27° C.): δ 171.0, 160.0, 156.3, 151.0, 136.9, 135.3, 130.8, 115.0, 66.5, 58.7, 44.4, 35.2, 23.7, 20.9, 7.4

(Example 38) Recycle Experiments

Benzyl alcohol was reacted in ethyl acetate solvent (0.5 M) by using 5% by mole of the trifluoroacetic acid-supporting polymer synthesized in Example 1. The yield at a reaction time of 1 hour was shown in the table below. The catalyst was filtered, and the reaction was conducted repeatedly. Even so, no decrease in catalytic activity was observed.

TABLE 6

| Number of Times of Recycle | 0 | 1 | 2 | 3 | 4 |
|---|---|---|---|---|---|
| Yield (%) | >99% | >99% | >99% | >99% | >99% |

The invention claimed is:

1. A polymer-supported metal, said metal being zinc, obtained by reacting, in a solvent, a zinc compound with a polymer of the following general formula (I):

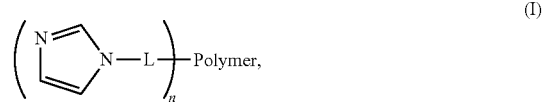

wherein
Polymer represents a polymer backbone,
L represents a linker,
n represents a natural number,
wherein a ratio of imidazolyl groups in the polymer (I) relative to zinc atoms is 4 to 8, and the imidazolyl group content in the polymer (I) is 1.25 mmol/g to 1.85 mmol/g.

2. The polymer-supported metal according to claim 1, wherein
in general formula (I), Polymer is a polystyrene, and L is a methylene group.

* * * * *